United States Patent [19]

Brecher

[11] Patent Number: 4,790,836

[45] Date of Patent: Dec. 13, 1988

[54] DISPOSABLE DIAPER

[76] Inventor: Arie Brecher, 23 Eilat Street, Holon 58 310, Israel

[21] Appl. No.: 860,881

[22] Filed: May 8, 1986

[30] Foreign Application Priority Data

May 14, 1985 [IL] Israel ..................................... 75189

[51] Int. Cl.⁴ .............................................. A61F 13/16
[52] U.S. Cl. ..................... 604/359; 604/364
[58] Field of Search ............... 604/359, 364, 367, 378, 604/385.1, 368, 364, 359

[56] References Cited

U.S. PATENT DOCUMENTS

| | | | |
|---|---|---|---|
| 2,418,907 | 4/1947 | Schreiber | 604/359 |
| 3,347,236 | 10/1967 | Torr | 604/364 |
| 3,490,454 | 1/1970 | Goldfarb et al. | 604/359 |
| 3,585,998 | 6/1971 | Hayford | 604/359 |
| 3,823,057 | 7/1974 | Roberts et al. | 604/359 |
| 3,875,942 | 4/1975 | Roberts et al. | 604/359 |
| 3,920,015 | 11/1975 | Wortham | 604/359 |
| 4,269,188 | 5/1981 | Nishizawa et al. | 604/378 |

*Primary Examiner*—John D. Yasko
*Assistant Examiner*—Sharon Rose
*Attorney, Agent, or Firm*—Benjamin J. Barish

[57] ABSTRACT

A disposable diaper for application to an infant in contact with the infant's skin, comprises a liquid absorbent core; a thin, continuous, water soluble film carried by the liquid absorbent core on the side thereof to be applied in contact with the infant's skin; a layer of a medicated powder between the water-soluble film and the liquid absorbent core; a liquid-permeable film between the layer of medicated powder and the absorbent core; and a liquid-impermeable film on the opposite side of the liquid absorbent core.

19 Claims, 1 Drawing Sheet

U.S. Patent  Dec. 13, 1988  4,790,836
FIG 1
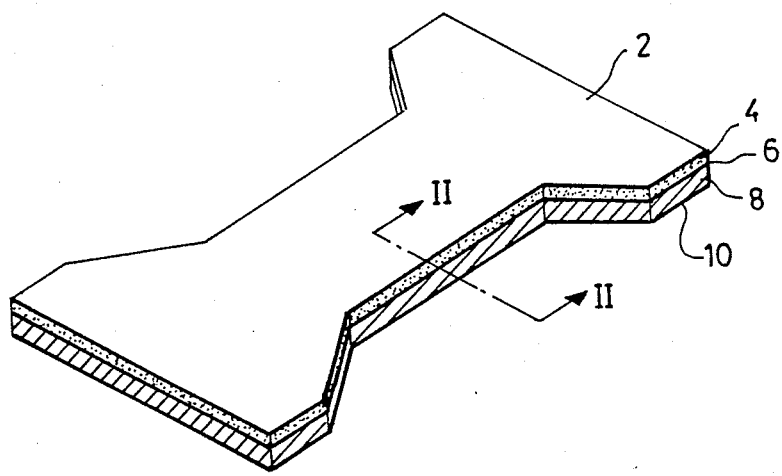
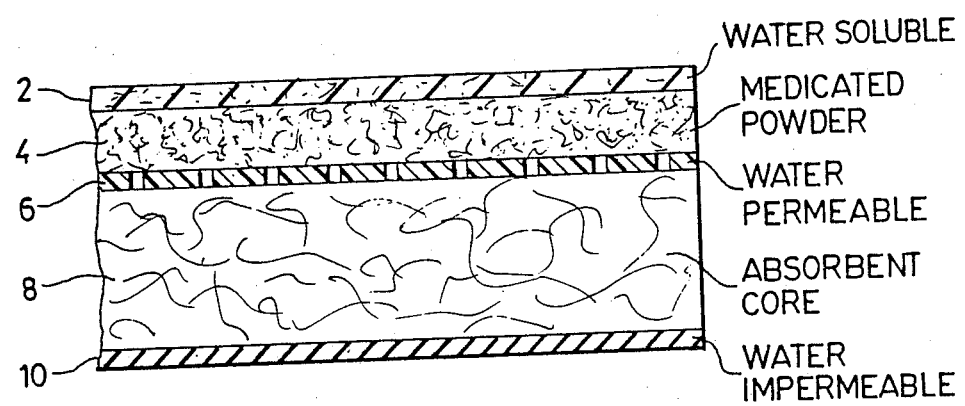
FIG. 2

DISPOSABLE DIAPER

BACKGROUND OF THE INVENTION

The present invention relates to diapers, and particularly to disposable diapers for one time use.

Many types of disposable diapers are presently available having a high capacity for absorbing liquids, but the prolonged contact of the infant's skin with the absorbed liquid irritates the infant's skin. Various disposable diaper constructions have been proposed to minimize this skin irritation. For example, U.S. Pat. No. 3,004,895 discloses a disposable diaper including an ammonia immobilizing agent covered by a gas-permeable liquid-impeding barrier such as to permit the ammonia from the urine to pass through the barrier into contact with the ammonia immobilizing agent where it is retained, while preventing the latter agent from directly contacting the infant's skin. Another disclosed technique, as illustrated by U.S. Pat. No. 2,119,610, provides the diaper with an outer protective covering of waterproof material formed with a plurality of perforations to permit the absorbent core to absorb the liquid. A further type, as illustrated by U.S. Pat. No. 3,585,998, provides the liquid absorbent core with a layer of pressure-rupturable capsules containing liquid baby oil. A still further type, as described in U.S. Pat. No. 3,875,942, provides the diaper with a layer of powder covered by a liquid imprevious sheet formed with a plurality of perforations permitting the powder to flow to the infant's skin. However, insofar as I am aware, none of the above types of disposable diapers has yet found widespread use.

An object of the present invention is to provide a new disposable diaper of the last-mentioned type for absorbing the liquids, while at the same time minimizing prolonged contact of the liquid with the infant's skin and reducing the possibility of irritation of the infant's skin by the liquid.

BRIEF SUMMARY OF THE INVENTION

According to the present invention, there is provided a disposable diaper for application to an infant in contact with the infant's skin, comprising: a liquid absorbent core; a thin, continuous homogeneous, water-soluble film which dissolves upon contact with water, the film being carried by the liquid absorbent core on the side thereof to be applied in contact with the infant's skin; and a continuous, homogeneous layer of a medicated powder applied as a separate and distinct layer between the water-soluble film and the liquid absorbent core.

In the described preferred embodiment, the disposable diaper further includes a liquid-permeable film between the layer of medicated powder and the liquid absorbent core; and a liquid-impermeable film on the opposite side of the liquid absorbent core.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a three dimensional view illustrating a preferred form of disposable diaper constructed in accordance with the invention:

FIG. 2 is a cross-sectional view along lines II—II of FIG. 1.

DESCRIPTION OF THE PREFERRED EMBODIMENT

The disposable diaper illustrated in the drawings comprises five layers, as follows: (a) a thin, continuous homogeneous water-soluble film 2 on the side of the diaper to be directly contacted by the infant's skin; (b) a medicated medicated powder layer 4; (c) a liquid-permeable film 6; (d) the absorbent core 8; and (e) a liquid-impermeable film 10.

The absorbent core 8 and the liquid-impermeable film 10 may be of conventional materials as commonly used today in disposable diapers; and the liquid-permeable film 6 may be a fabric, e.g. a non-woven fabric, or a plastic sheet such as polyethylene formed with liquid-permeable openings, as also used in some types of diapers.

The medicated powdered layer 4 may be one of the known medicated powder formulations which are commonly supplied in separate containers for application to the infant's skin after a diaper has been removed in order to promote drying and to reduce skin irritation. In this case, however, the medicated powder is applied as a separate and distinct layer to the diaper.

It will thus be seen that when the diaper is applied to the infant, the continuous, water-soluble film 2 maintains the medicated powder of layer 4 intact and out of contact with the infant's skin; but as soon as the infant wets the diaper, film 2 is dissolved. This permits the liquid to pass via the medicated powder layer 4 and the liquid-permeable film 6 and to be absorbed in the absorbant core 8, while at the same time the medicated powder of layer 4 is brought into direct contact with the infant's skin to promote drying of the infant's skin and also to medicate it.

Thus, the possiblility of irritating the infant's skin by prolonged contact with the liquid is very substantially reduced. At the same time the need to immediately remove the diaper and to apply powder, oil, cream or other material to the baby's skin in order to prevent skin irritation is obviated.

The thin, continuous film 2 may be of any suitable water-soluble material. Preferred examples are gelatin, pectin, and methyl cellulose.

Following are two examples of medicated powder formulations (by weight) which may be used for layer 4.

EXAMPLE 1 aluminum dihydroxy allantoinate: 0.2%
p-chloro-M-xylenol: 0.5%
cellulose: 45.0%
corn starch: remainder

EXAMPLE 2 magnesium carbonate: 3.5%
corn starch: 96.5%

While the invention has been described with respect to a preferred embodiment it will be appreciated that many variations, modifications, and other applications of the invention may be made.

What is claimed is:

1. A disposible diaper for application to an infant in contact with the infant's skin, comprising:
a liquid absorbent core;
a continuous, homogeneous water-soluble film which dissolves upon contact with water, said film being carried by said liquid absorbent core on one side thereof to be applied in contact with the infant's skin;

and a continuous, homogeneous layer of medicated powder applied as a separate and distinct layer between said water soluble film and said liquid absorbent core.

2. The diaper according to claim 1, further including: a liquid-permeable film between said layer of medicated power and said liquid absorbent core.

3. The diaper according to claim 2, further including a liquid-impermeable film on the side of said liquid absorbent core opposite to that of said layer of medicated powder.

4. The diaper according to claim 1, wherein said water-soluble film is gelatin.

5. The diaper according to claim 1, wherein said water soluble film is pectin.

6. The diaper according to claim 1, wherein said water-soluble film is methyl cellulose.

7. The diaper according to claim 1, wherein said medicated powder is a mixture of aluminum dihydroxy allantoinate, p-chloro-M-xylenol, cellulose, and corn starch.

8. The diaper according to claim 1, wherein said medicated powder is a mixture of magnesium carbonate and corn starch.

9. A disposable diaper for application to an infant in contact with the infant's skin, comprising:
a liquid absorbent core;
a thin, continuous, water-soluble film which dissolves upon contact with water, said film being carried by said liquid absorbent core on the side thereof to be applied in contact with the infant's skin;
a continuous, homogeneous layer of medicated powder applied as a separate and distinct layer between said water soluble film and said liquid absorbent core;
and a liquid-permeable film between said layer of medicated powder and said liquid absorbent core.

10. The diaper according to claim 9, further including a liquid-impermeable film on the side of said liquid absorbent core opposite to that of said layer of medicated powder.

11. The diaper according to claim 9, wherein said water-soluble film is gelatin.

12. The diaper according to claim 9, wherein said water-soluble film is pectin.

13. The diaper according to claim 9, wherein said water-soluble film is methyl cellulose.

14. The diaper according to claim 9, wherein said medicated powder is a mixture of aluminum dihydroxy allantoinate, p-chloro-M-xylenol, cellulose, and corn starch.

15. The diaper according to claim 9, wherein said medicated powder is a mixture of magnesium carbonate and corn starch.

16. A disposable diaper for application to an infant in contact with the infant's skin, comprising:
a liquid absorbent core;
a thin, continuous, homogeneous water-soluble film which dissolves upon contact with water, said film being carried by said liquid absorbent core on one side thereof to be applied in contact with the infant's skin;
a continuous, homogeneous layer of medicated powder applied as a separate and distinct layer between said water-soluble film and said liquid absorbent core;
a liquid-permeable film between said layer of medicated powder and said absorbent core;
and a liquid-impermeable film on the opposite side of said absorbent core.

17. The diaper according to claim 16, wherein said water-soluble film is gelatin.

18. The diaper according to claim 16, wherein said water-soluble film is pectin.

19. The diaper according to claim 16, wherein said water-soluble film is methyl cellulose.

* * * * *